United States Patent
Goto et al.

(10) Patent No.: US 10,414,848 B2
(45) Date of Patent: Sep. 17, 2019

(54) LIVING RADICAL POLYMERIZATION INITIATOR, METHOD FOR PRODUCING POLYMER, AND POLYMER

(71) Applicants: KYOTO UNIVERSITY, Kyoto-shi, Kyoto (JP); GODO SHIGEN CO., LTD., Chuo-ku, Tokyo (JP)

(72) Inventors: Atsushi Goto, Kyoto (JP); Michihiko Miyamoto, Chiba (JP); Hiroto Komatsu, Chiba (JP); Yu Yamaguchi, Chiba (JP); Takuya Jitsukawa, Chiba (JP)

(73) Assignees: KYOTO UNIVERSITY, Kyoto (JP); GOOD SHIGEN CO., LTD, Tokyo (JP)

(*) Notice: Subject to any disclaimer, the term of this patent is extended or adjusted under 35 U.S.C. 154(b) by 275 days.

(21) Appl. No.: 15/508,313

(22) PCT Filed: Aug. 7, 2015

(86) PCT No.: PCT/JP2015/003991
§ 371 (c)(1),
(2) Date: Mar. 2, 2017

(87) PCT Pub. No.: WO2016/035258
PCT Pub. Date: Mar. 10, 2016

(65) Prior Publication Data
US 2017/0306073 A1    Oct. 26, 2017

(30) Foreign Application Priority Data

Sep. 2, 2014 (JP) .................................. 2014-178384

(51) Int. Cl.
*C07C 69/63* (2006.01)
*C07C 69/65* (2006.01)
(Continued)

(52) U.S. Cl.
CPC .......... *C08F 293/005* (2013.01); *C07C 69/63* (2013.01); *C07C 69/635* (2013.01); *C07C 69/65* (2013.01); *C07C 69/73* (2013.01)

(58) Field of Classification Search
CPC ....... C07C 69/63; C07C 69/65; C07C 69/635; C07C 69/73; C08F 8/00; C08F 293/005
(Continued)

(56) References Cited

FOREIGN PATENT DOCUMENTS

| JP | 2009203359 A | 9/2009 |
| JP | 2010024263 A | 2/2010 |
| JP | 2013072069 A | 4/2013 |

OTHER PUBLICATIONS

Yaling Zhu, et al., "New Dual Initiators to Combine Quasiliving Carbocationic Polymerization and Atom Transfer Radical Polymerization", Macromolecules, 2010,43, pp. 7048-7055.*
(Continued)

*Primary Examiner* — William K Cheung
(74) *Attorney, Agent, or Firm* — Holtz, Holtz & Volek

(57) ABSTRACT

A living radical polymerization initiator represented by the following:

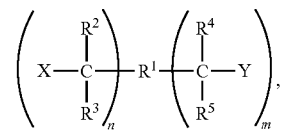

wherein, $R^1$ represents an aromatic, an alkylcarbonyl, an alkoxycarbonyl, an aminocarbonyl, an alkylaminocarbonyl, a dialkylaminocarbonyl, an arylcarbonyl, an alkylsulfonyl, an aryl sulfonyl or combinations thereof; $R^2$, $R^3$, $R^4$ and
(Continued)

$R^5$ are a hydrogen, an aliphatic, an aromatic, an alkylcarbonyl, an alkoxycarbonyl, an aminocarbonyl, an alkylaminocarbonyl, a dialkylaminocarbonyl, an arylcarbonyl, a carboxy, an alkylsulfonyl or an aryl sulfonyl; X and Y are a halogen; m and n are an integer of 1 or more, and

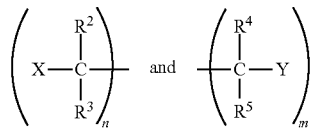

are non-symmetrical so that X and Y have different reactivities to initiate a living radical polymerization.

11 Claims, 3 Drawing Sheets

(51) Int. Cl.
  *C07C 69/73* (2006.01)
  *C07C 69/635* (2006.01)
  *C08F 8/00* (2006.01)
  *C08F 293/00* (2006.01)
(58) Field of Classification Search
  USPC ............................................. 526/206
  See application file for complete search history.

(56) References Cited

OTHER PUBLICATIONS

Extended European Search Report (EESR) dated May 4, 2018 issued in counterpart European Application No. 15838864.5.

Japanese Office Action (and English Language translation thereof) dated Oct. 16, 2018 issued in counterpart Japanese Application No. 2014-178384.
Clausen, et al., "New Coupling Reactions of Some Acyl Chlorides with Samarium Diiodide in the Presence of Samarium: Carbinols from Three Acyl Units", European Journal of Organic Chemistry, Nov. 1, 2000, vol. 2000, No. 22, pp. 3799-3806.
International Search Report (ISR) and Written Opinion dated Oct. 13, 2015 issued in International Application No. PCT/JP2015/003991.
Yaling Zhu, et al., "Effect of Structure on Cationic Initiation Efficiency of a Carbocatonic/ATRP Dual Initiator", Macromolecules, 2012, 45, pp. 1217-1221.
Yaling Zhu, et al., "New Initiators to Combine Quasiliving Carbocationic Polymerization and Atom Transfer Radical Polymerization", Polymer Preprints, 2009, 50(2), pp. 535-536.
Miho Tanishima, et al., "Macromolecular Architectures Designed by Living Radical Polymerization with Organic Catalysts", Polymers, 2014, 6, pp. 311-326.
Lin Lei, et al., "Systematic Study on Alkyl Iodide Initiators in living Radical Polymerization with Organic Catalysts", Macromolecules, 2014, 47, pp. 6610-6618.
Atsushi Goto, et al., "Yoso o Mochiita Yuki Shokubai-gata Living Radical Jugo: Yoso no Tokusei o Katsuyo shita Kobunshi no Seigyo Gosei", SIS Report, 2014, (17), pp. 5-8.
Atsushi Goto, et al., "Living Radical Polymerization with Organic Catalysts under Thermal Heating and Photo Irradiation", Japanese Journal of Polymer Science and Technology, 2015, 72(5), pp. 199-207.
Atsushi Goto, "Yuki Shokubai o Mochiita Living Radical Jugo no Kaihatsu to Tenkai", Tokai Symposium Koen Yoshishu, 2014, pp. 1-8.
Atsushi Goto, et al., "Yuki Bunshi Shokubai o Mochiita Living Radical Jugo no Shokubai Sekkei", Polymer Preprints, Japan, 2014, 63(2), pp. 4442 to 4443.
V. Percec, et al., "Metal-Catalyzed Living Radical Graft Copolymerization of Olefins Initiated from the Structural Defects of Poly(vinyl chloride)", Journal of Polymer Science, Part A, 2001, 39, pp. 1120-1135.

* cited by examiner

LIVING RADICAL POLYMERIZATION INITIATOR, METHOD FOR PRODUCING POLYMER, AND POLYMER

This applications a U.S. National stage application of International Application No. PCT/JP2015/003991, filed on Aug. 7, 2015. This U.S. National stage application claims priority under 35 U.S.C. § 119(a) to Japanese Patent Application No. 2014-178384, filed in Japan on Sep. 2, 2014, the entire contents of which are hereby incorporated herein by reference.

TECHNICAL FIELD

The present invention relates to a polymerization initiator used for living radical polymerization, a method for producing a polymer, and a polymer produced by using them.

BACKGROUND ART

As a method for obtaining a vinyl polymer based on polymerization of a vinyl monomer, a radical polymerization method is conventionally known. The radical polymerization method has a disadvantage that it is generally difficult to control the molecular weight of a vinyl polymer to be obtained.

Furthermore, there is also a disadvantage that, as the vinyl polymer to be obtained is a mixture of compounds with various molecular weights, it is difficult to obtain a vinyl polymer with narrow molecular weight distribution.

Specifically, even when the reaction is controlled, the ratio (Mw/Mn) between weight average molecular weight (Mw) and number average molecular weight (Mn) can be only reduced to 2 to 3 or so.

As a method for overcoming the above disadvantages, a living radical polymerization method has been developed since 1990. Namely, according to the living radical polymerization method, it is possible to control the molecular weight and also possible to obtain a polymer with a narrow molecular weight distribution.

Specifically, since it is possible to obtain easily a polymer which has Mw/Mn of 2 or less, the method receives great attention as a method for producing a polymer that is used for a cutting edge field like nano technology (see, Patent Literature 1, for example).

CITATION LIST

Patent Literature

Patent Literature 1: JP 2009-203359 A

SUMMARY OF INVENTION

Technical Problem

Meanwhile, the conventional radical polymerization method described above involves a reaction system in which the polymerization reaction progresses for one initiating group of a polymerization initiator. However, it would be preferable to have a reaction system in which a different polymerization reaction is carried out for a plurality of initiating groups.

Accordingly, the present invention is devised in view of the problems described above, and an object of the present invention is to provide a living radical polymerization initiator which has two halogen atoms different from each other in reactivity and enables different polymerization reactions to proceed in two directions by having each of the halogen atoms as a initiating group, a method for producing a polymer, and a polymer produced by using them.

Solution to Problem

To solve the problems described above, the inventors of the present invention invented a living radical polymerization initiator which has two halogen atoms different from each other in reactivity and enables different polymerization reactions to proceed in two directions by having each of the halogen atoms as a initiating group, a method for producing a polymer, and a polymer produced by using them.

A living radical polymerization initiator according to a first invention is a living radical polymerization initiator which consists of the following general formula (1):

[Chemical Formula 1]

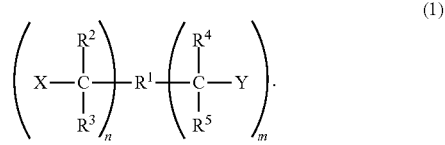

Herein, $R^1$ represents an organic group which is linkable with two or more other organic groups, and is an aliphatic group having 1 to 12 carbon atoms, an aromatic group, an alkylcarbonyl group having 1 to 12 carbon atoms, an alkoxycarbonyl group having 1 to 12 carbon atoms, an aminocarbonyl group, an alkylaminocarbonyl group having 1 to 12 carbon atoms, a dialkylaminocarbonyl group having 1 to 12 carbon atoms, an arylcarbonyl group, an alkylsulfonyl group having 1 to 12 carbon atoms, an aryl sulfonyl group, or an organic group in which two or more of those groups are combined, $R^2$, $R^3$, $R^4$ and $R^5$ are a hydrogen atom or an organic group selected from an aliphatic group having 1 to 12 carbon atoms, an aromatic group, an alkylcarbonyl group having 1 to 12 carbon atoms, an alkoxycarbonyl group having 1 to 12 carbon atoms, an aminocarbonyl group, an alkylaminocarbonyl group having 1 to 12 carbon atoms, a dialkylaminocarbonyl group having 1 to 12 carbon atoms, an arylcarbonyl group, a carboxy group, an alkylsulfonyl group having 1 to 12 carbon atoms, and an aryl sulfonyl group, X and Y are a halogen atom, m and n are an integer of 1 or more, and the X and Y are in a state in which they are different from each other in reactivity with a monomer.

In the living radical polymerization initiator according to a second invention, in the first invention, the halogen atom is iodide, chloride, or bromide.

A method for producing a polymer according to a third invention is a method for producing a polymer by using the living radical polymerization initiator according to the first or second invention, including: a first polymerization step in which, for only one halogen atom of the X or Y of the living radical polymerization initiator, a living radical polymerization reaction in which the living radical polymerization reaction initiator is mixed with a monomer with an unsaturated bond and the reaction is carried out at a reaction condition depending on a type of the monomer one or more times while changing in order the type of the monomer to be mixed to obtain a first product; and a second polymerization step in which, for both halogen atoms of the X and Y contained in the first product, at least one type of the monomer is subjected to a living radical polymerization reaction in an order and at a reaction condition depending on a type of the monomer to obtain a final product.

In the method for producing a polymer according to a fourth invention, in the third invention, the first polymerization step and the second polymerization step are carried out by using a catalyst and the first polymerization step and the second polymerization step are carried out such that at least one of reaction temperature and the type of the catalyst is changed depending on the type of the monomer.

In the method for producing a polymer according to a fifth invention, in the fourth invention, the catalyst is a transition metal complex-based catalyst which is used for an atom transfer radical polymerization, a catalyst consisting of a compound containing at least one center element selected from phosphorus, nitrogen, carbon, oxygen, germanium, tin, and antimony and a halogen atom bound to the center element, which is used for reversible chain transfer catalyst polymerization, an organic amine compound catalyst used for reversible complexation mediated polymerization, or a catalyst in which, as a non-metal compound having an ionic bond with a halide ion, a non-metal atom in the non-metal compound is in a cation state and forms an ionic bond with the halide ion.

In the method for producing a polymer according to a sixth invention, in any one of the third to fifth invention, the first polymerization step and the second polymerization step are carried out at 180° C. or lower.

In the method for producing a polymer according to a seventh invention, in any one of the third to sixth invention, the first polymerization step and the second polymerization step are carried out for a reaction time of 30 minutes or longer and 24 hours or shorter.

A polymer according to the eighth invention is produced by using the method for producing a polymer according to any one of the third to seventh inventions.

Advantageous Effects of Invention

According to the present invention consisting of the above constitutions, it is possible to provide a living radical polymerization initiator which has two halogen atoms different from each other in reactivity and enables different polymerization reactions to proceed in two directions by having each of the halogen atoms as a initiating group, a method for producing a polymer, and a polymer produced by using them.

DESCRIPTION OF EMBODIMENTS

Figure 1:
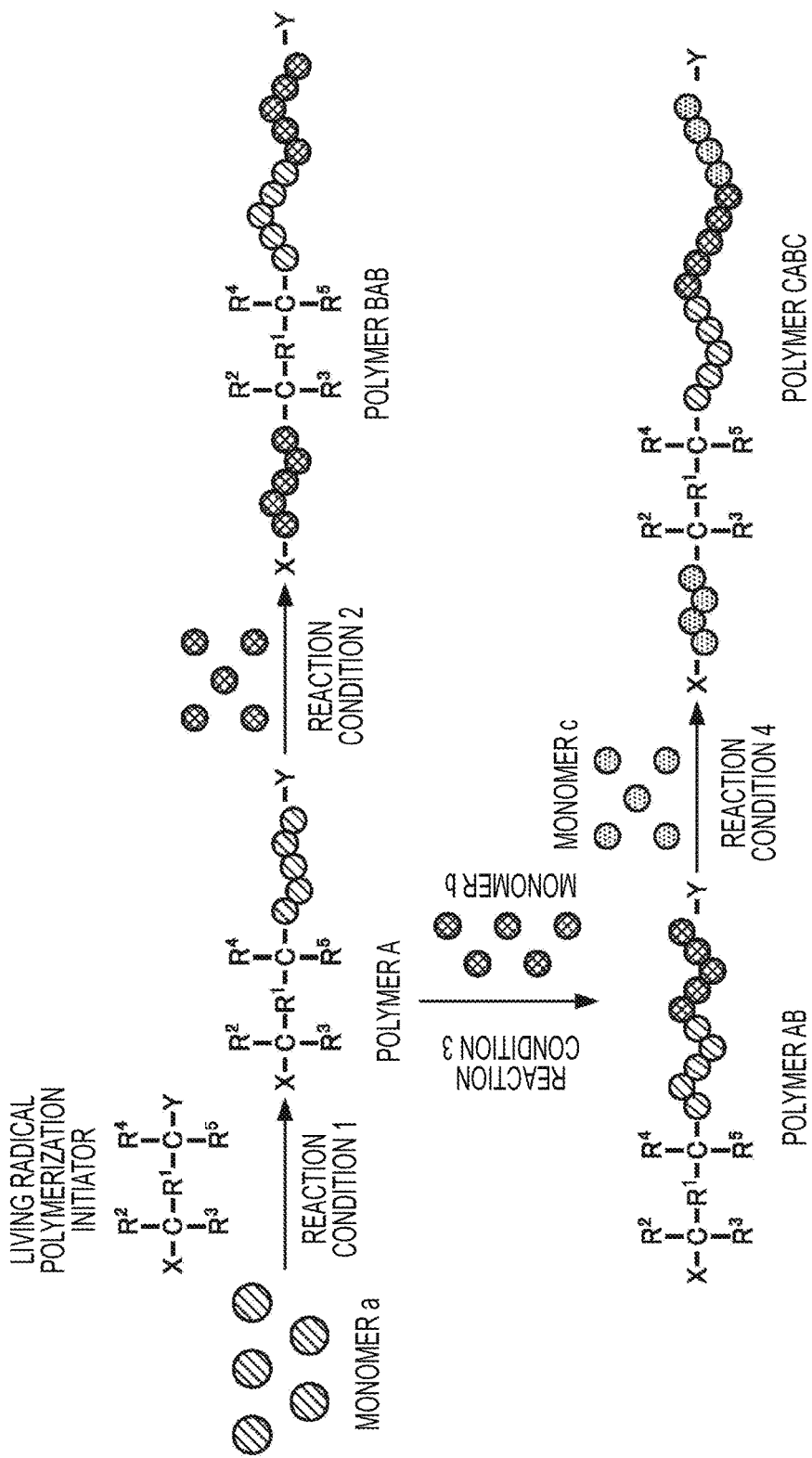
FIG. 1 is a schematic diagram illustrating a basic reaction in a method for producing a polymer according to an embodiment of the present invention.

Hereinbelow, a living radical polymerization initiator according to an embodiment of the present invention and a method for producing a polymer by using it are described in detail.

[Living Radical Polymerization Initiator]
(1) Chemical Formula of Living Radical Polymerization Initiator The living radical polymerization initiator according to this embodiment has a structure represented by the chemical formula (1), and it has two halogen atoms different from each other in reactivity.

[Chemical Formula 1]

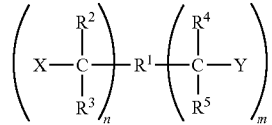

(1)

In the above chemical formula (1), $R^1$ is an organic group with a valency of two or more, i.e., an organic group which is linkable with two or more other organic groups, and examples thereof include an aliphatic group having 1 to 12 carbon atoms, an aromatic group, an alkylcarbonyl group having 1 to 12 carbon atoms, an alkoxycarbonyl group having 1 to 12 carbon atoms, an aminocarbonyl group, an alkylaminocarbonyl group having 1 to 12 carbon atoms, a dialkylaminocarbonyl group having 1 to 12 carbon atoms, an arylcarbonyl group, an alkylsulfonyl group having 1 to 12 carbon atoms, an aryl sulfonyl group, and an organic group in which two or more of those groups are combined.

Furthermore, each of $R^2$, $R^3$, $R^4$ and $R^5$ is a hydrogen atom or an organic group selected from an aliphatic group having 1 to 12 carbon atoms, an aromatic group, an alkylcarbonyl group having 1 to 12 carbon atoms, an alkoxycarbonyl group having 1 to 12 carbon atoms, an aminocarbonyl group, an alkylaminocarbonyl group having 1 to 12 carbon atoms, a dialkylaminocarbonyl group having 1 to 12 carbon atoms, an arylcarbonyl group, an alkylsulfonyl group having 1 to 12 carbon atoms, and an aryl sulfonyl group, X and Y are a halogen atom, and m and n are an integer of 1 or more. The left and right structures of the linking group $R^1$ in the chemical formula (1) are non-symmetrical so that the halogen atoms X and Y have different reactivities.

(2) Linking Group

The linking group $R^1$ is not particularly limited as long as it is an organic group which is linkable with two or more other organic groups. Specific examples thereof include an aliphatic group, an aromatic group, an alkylcarbonyl group having 1 to 12 carbon atoms, an alkoxycarbonyl group having 1 to 12 carbon atoms, an aminocarbonyl group, an alkylaminocarbonyl group having 1 to 12 carbon atoms, a dialkylaminocarbonyl group having 1 to 12 carbon atoms, an arylcarbonyl group, an alkylsulfonyl group having 1 to 12 carbon atoms, an aryl sulfonyl group, and an organic group in which two or more of those groups are combined.

The linking group $R^1$ may have a substituent group, and in a case in which it has a substituent group, the number of the substituent groups is not particularly limited as long as the substitution can be made, and the number is 1 or more.

As for the group which may be substituted on the linking group $R^1$, a halogen atom, a linear or non-linear alkyl group having 1 to 12 carbon atoms which may be substituted, an aromatic group which may be substituted, a non-aromatic heterocyclic group which may be substituted, a carboxy group, a linear or non-linear alkoxy group having 1 to 12 carbon atoms, a cyano group, a nitro group, and the like can be mentioned.

As for the aliphatic group, a linear or non-linear alkyl group having 1 to 12 carbon atoms which may be substituted can be mentioned.

In a case in which the aliphatic group is substituted, the number of the substituent group is not particularly limited, and it is 1 or more.

Furthermore, as for the group which may be substituted on the aliphatic group, a halogen atom, a linear or non-linear alkyl group having 1 to 12 carbon atoms which may be substituted, an aromatic group which may be substituted, a non-aromatic heterocyclic group which may be substituted, a linear or non-linear alkoxy group having 1 to 12 carbon atoms, a cyano group, a nitro group, and the like can be mentioned.

As for the aromatic group, an aromatic hydrocarbon cyclic group or an aromatic heterocyclic group can be mentioned, and specific examples thereof include a phenyl group, a biphenylyl group, a terphenylyl group, a naphthyl group, a binaphthylyl group, an azulenyl group, an anthracenyl group, a phenanthrenyl group, a furarenyl group, a furyl group, a thienyl group, a pyrrolyl group, a pyrazolyl group, an imidazolyl group, an isoxazolyl group, a thiazolyl group, a tidiazolyl group, a pyridyl group, a benzofuranyl group, an indolyl group, a benzothiazolyl group, and a carbazolyl group.

The aromatic group may be substituted, and in that case, the number of the substituent group is not particularly limited as long as the substitution can be made, and it is 1 or more.

Furthermore, as for the group which may be substituted on the aromatic group, a halogen atom, a linear or non-linear alkyl group having 1 to 12 carbon atoms which may be substituted, an aromatic group which may be substituted, a non-aromatic heterocyclic group which may be substituted, a carboxy group, a linear or non-linear alkoxy group having 1 to 12 carbon atoms, a cyano group, a nitro group, and the like can be mentioned.

(3) $R^2$ to $R^5$

As for the aliphatic group, a linear or non-linear alkyl group having 1 to 12 carbon atoms which may be substituted can be mentioned.

In a case in which the aliphatic group is substituted, number of the substituent group is not particularly limited as long as the substitution can be made, and it is 1 or more.

Furthermore, as for the group which may be substituted on the aliphatic group, a halogen atom, a linear or non-linear alkyl group having 1 to 12 carbon atoms which may be substituted, an aromatic group which may be substituted, a non-aromatic heterocyclic group which may be substituted, a linear or non-linear alkoxy group having 1 to 12 carbon atoms, a cyano group, a nitro group, and the like can be mentioned.

As for the aromatic group, an aromatic hydrocarbon cyclic group or an aromatic heterocyclic group can be mentioned, and specific examples thereof include a phenyl group, a biphenylyl group, a terphenylyl group, a naphthyl group, a binaphthylyl group, an azulenyl group, an anthracenyl group, a phenanthrenyl group, a furarenyl group, a furyl group, a thienyl group, a pyrrolyl group, a pyrazolyl group, an imidazolyl group, an isoxazolyl group, a thiazolyl group, a tidiazolyl group, a pyridyl group, a benzofuranyl group, an indolyl group, a benzothiazolyl group, and a carbazolyl group.

The aromatic group may be substituted, and in that case, the number of the substituent group is not particularly limited as long as the substitution can be made, and it is 1 or more.

Furthermore, as for the group which may be substituted on the aromatic group, a halogen atom, a linear or non-linear alkyl group having 1 to 12 carbon atoms which may be substituted, an aromatic group which may be substituted, a non-aromatic heterocyclic group which may be substituted, a carboxy group, a linear or non-linear alkoxy group having 1 to 12 carbon atoms, a cyano group, a nitro group, and the like can be mentioned.

Furthermore, as for the arylcarbonyl group, a benzoyl group, a 1-naphthoyl group, a 2-naphthoyl group, a 2-pyridylcarbonyl group, a 3-pyridylcarbonyl group, a 4-pyridylcarbonyl group, and the like can be mentioned.

Furthermore, as for the aryl sulfonyl group, a benzene sulfonyl group, a toluene sulfonyl group, and the like can be mentioned.

Furthermore, X and Y in the chemical formula (1) represent a halogen atom, and they are preferably chloride, bromide, or iodide, and more preferably iodide.

Since the aforementioned living radical polymerization initiator according to the present invention has two halogen atoms that are different from each other in reactivity as an initiating group, by suitably adjusting the reaction conditions, the living radical polymerization reaction different for each initiating group is allowed to occur.

[Method for Producing a Polymer]

Next, descriptions are given for the method for producing a polymer of a radical polymerizable monomer which is obtained by carrying out a living radical polymerization by using the aforementioned living radical polymerization initiator.

(1) Basic Reaction

The method for producing a polymer according to this embodiment is achieved by performing a basic reaction illustrated in FIG. 1 with use of the aforementioned living radical polymerization initiator. FIG. 1 is a schematic diagram illustrating a basic reaction in a method for producing a polymer according to an embodiment of the invention. In FIG. 1, a, b, and c each represent a radical reactive polymerizable monomer having an unsaturated bond, and each of them may be a different monomer or the same monomer. Furthermore, A, B, and C each represent a polymer block.

According to the basic reaction illustrated in FIG. 1, as a first step, the polymerization reaction of a radical polymerizable monomer is carried out one or more times by having one of the halogen atoms as an initiating group while the type of a monomer to be mixed is changed in order, and then as a second step, the polymerization reaction is carried out to produce a polymer by using the other halogen atom remaining in the skeleton of an initiator as an initiator.

Herein, the halogen atom Y in the living radical polymerization initiator of FIG. 1 is designed such that it has a higher reactivity than the halogen atom X.

Furthermore, since each of the reaction conditions 1 to 4 has a different reaction condition, one or more of the reaction temperature, reaction time, presence or absence of a catalyst, and the type of the catalyst is different.

According to the reaction of FIG. 1, the monomer a and the living radical polymerization initiator are first reacted with each other at reaction condition 1. The reaction condition 1 is set such that the living radical polymerization progresses only with the halogen atom Y which has a higher reactivity among the living radical polymerization initiators.

Accordingly, polymer A in which a plurality of the monomers A are polymerized to the halogen atom Y of the living radical polymerization initiator is produced.

The polymer A is then subjected to a living radical polymerization reaction with the monomer b. By changing the reaction condition, a different polymer can be obtained.

Specifically, by reacting the polymer A with the monomer b under the reaction condition 2 in which the reaction is allowed to occur, not only with the halogen atom Y having a high reactivity, but also with the halogen atom X having a low reactivity, polymer BAB, in which a plurality of the monomers b are polymerized at each side of the halogen atom X and the halogen atom Y of the polymer A, is generated.

Incidentally, by reacting the polymer A with the monomer b under the reaction condition 3 in which the reaction is allowed to occur only with the halogen atom Y having a high reactivity, polymer AB, in which a plurality of the monomers b are polymerized at the halogen atom Y side of the polymer A, is generated.

As described above, according to the aforementioned basic reaction, any one halogen atom remains unreacted in the first step of the reaction, and by varying the reaction temperature or adding a different catalyst in the second step and the third step, the remaining halogen atom reacts as an initiating group with the monomer.

It is also possible to carry out an additional living radical polymerization reaction for the polymer BAB or the polymer AB which is obtained as described above.

For example, by reacting the polymer AB with the monomer c under the reaction condition 4 in which both the halogen atom X and the halogen atom Y react, polymer CABC in which a plurality of the monomers c are polymerized at each side of the halogen atom X and the halogen atom Y of the polymer AB is generated. It is evident that the polymer ABC can be obtained by carrying out the reaction under the reaction condition in which the monomer c reacts with the halogen atom Y side of the polymer AB and a different living polymerization reaction is allowed to proceed additionally with the polymer CABC or the polymer ABC.

(2) Radical Polymerizable Monomer

The radical polymerizable monomer used for the aforementioned reaction is a monomer having an unsaturated bond which allows radical polymerization in the presence of an organic radical. The unsaturated bond may be a triple bond rather than a double bond. Namely, for the method for producing a polymer according to the present embodiment, any one of conventionally known monomers allowing a living radical polymerization can be used.

Such radical polymerizable monomer is specifically a monomer which is referred to as a vinyl monomer. The vinyl monomer is a general name of monomers that are represented by general formula "$CH_2=CR^5R^6$".

With regard to the above general formula, a monomer in which $R^5$ is methyl and $R^6$ is carboxylate is referred to as a methacrylate-based monomer, and it can be desirably used in the present invention, Specific examples of the methacrylate-based monomer include methyl methacrylate, ethyl methacrylate, propyl methacrylate, n-butyl methacrylate, t-butyl methacrylate, hexyl methacrylate, 2-ethylhexyl methacrylate, nonyl methacrylate, benzyl methacrylate, glycidyl methacrylate, cyclohexyl methacrylate, lauryl methacrylate, n-octyl methacrylate, 2-methoxyethyl methacrylate, butoxyethyl methacrylate, methoxytetraethylene glycol methacrylate, 2-hydroxyethyl methacrylate, 2-hydroxypropyl methacrylate, 3-chloro-2-hydroxypropyl methacrylate, tetrahydrofurfuryl methacrylate, 2 hydroxy 3-phenoxypropyl methacrylate, diethylene glycol methacrylate, polyethylene glycol methacrylate, and 2-(dimethylamino)ethyl methacrylate.

Furthermore, methacrylic acid can be also used.

Furthermore, a methacrylate with an ion liquid property like 2-(N,N-diethyl-N-methylamino)ethyl methacrylate+/trifluorosulfonyl iminium (N(CF3SO2)2-) salt, 2-(N-ethyl-N-methyl-N-hydrogenated amino)ethyl methacrylate+/trifluorosulfonyl iminium (N(CF3SO2)2-) salt, 1-ethyl-3-methylimidazolium methacrylate+/fluorohydrogenation ((FH)nF—) salt, and N-ethyl-N-methylpyrrolidinium methacrylate+/fluorohydrogenation ((FH)nF—) salt can be used.

With regard to the above general formula of a vinyl monomer, a monomer in which R5 is hydrogen and R6 is carboxylate is referred to as an acrylate-based monomer, and it can be desirably used in the present invention.

Specific examples of the acrylate-based monomer include methyl acrylate, ethyl acrylate, propyl acrylate, n-butyl acrylate, t-butyl acrylate, hexyl acrylate, 2-ethylhexyl acrylate, nonyl acrylate, benzyl acrylate, glycidyl acrylate, cyclohexyl acrylate, lauryl acrylate, n-octyl acrylate, 2-methoxyethyl acrylate, butoxyethyl acrylate, methoxytetraethylene glycol acrylate, 2-hydroxyethyl acrylate, 2-hydroxypropyl acrylate, 3-chloro 2-hydroxypropyl acrylate, tetrahydrofurfuryl acrylate, 2-hydroxy 3-phenoxypropyl acrylate, diethylene glycol acrylate, polyethylene glycol acrylate, and 2-(dimethylamino)ethyl acrylate.

Furthermore, acrylic acid can be also used.

Furthermore, an acrylate with ion liquid property like 2-(N,N-diethyl-N-methylamino)ethyl acrylate+/trifluorosulfonyl iminium (N(CF3SO2)2-) salt, 2-(N-ethyl-N-methyl-N-hydrogenated amino)ethyl acrylate+/trifluorosulfonyl iminium (N(CF3SO2)2-) salt, 1-ethyl-3-methylimidazolium acrylate+/fluorohydrogenation ((FH)nF—) salt, and N-ethyl-N-methylpyrrolidinium acrylate+/fluorohydrogenation (FH)nF—) salt can be used.

Controlling the living radical polymerization of an acrylate is difficult in general. However, the control can be made according to the present invention. When a phosphorus-based catalyst is used, in particular, the polymerization of an acrylate can be desirably controlled.

With regard to the above general formula of a vinyl monomer, a monomer in which $R^5$ is hydrogen and $R^6$ is phenyl corresponds to styrene and it can be desirably used in the present invention.

Furthermore, a monomer in which $R^6$ is phenyl or a phenyl derivative corresponds to a styrene derivative and it can be desirably used in the present invention. Specific examples thereof include o-, m-, p-methoxystyrene, o-, m-, p-styrene sulfonic acid, and the like.

Furthermore, vinyl naphthalene in which $R^6$ is an aromatic can be also mentioned.

With regard to the above general formula of a vinyl monomer, a monomer in which R5 is hydrogen and R6 is alkyl corresponds to alkylene and it can be desirably used in the present invention.

For the present invention, a monomer having two or more vinyl groups can be also used. Specific examples thereof include a diene-based compound (for example, butadiene and isoprene), a compound with two allyl groups (for example, diallyl phthalate), dimethacrylate with two methacryls (for example, ethylene glycol dimethacrylate), and diacrylate with two acryls (for example, ethylene glycol diacrylate).

For the present invention, a vinyl monomer other than those described above can be also used. Specific examples thereof include vinyl esters (for example, vinyl acetate, vinyl propionate, vinyl benzoate, and vinyl acetate), a styrene derivative other that those described above (for example, α-methylstyrene), vinylketones (for example, vinyl ethyl ketone, vinyl hexyl ketone, and methyl isopropenyl ketone), an N-vinyl compound (for example, N-vinyl pyrrolidone, N-vinyl pyrrole, N-vinyl carbazole, and N-vinyl indole), (meth)acrylamide and a derivative thereof (for example, N-isopropyl acrylamide, N-isopropyl methacrylamide, N,N-dimethyl acrylamide, N,N-dimethyl methacrylamide, N-methylol acrylamide, and N-methylolmethacrylamide), acrylonitrile, methacrylonitrile, maleic acid and a derivative thereof (for example, maleic anhydride), vinyl halides (for example, vinyl chloride, vinylidenechloride, tetrachloroethylene, hexachloropropylene, and vinyl fluoride), and olefins (for example, ethylene, propylene, 1-hexene, and cyclohexene).

Those monomers may be used either singly or in combination of two or more types. Furthermore, two or more types of a monomer may be added simultaneously at the time of initiating the reaction of the first step, or they may be added to each step of the reaction.

(3) Catalyst

For a monomer which is arbitrarily selected, an arbitrarily selected catalyst of the present invention may be added, if necessary. It is possible not to have any catalyst. However, by adding the catalyst, the reaction progresses more favorably. A combination of the type of the monomer and the type of the catalyst of the present invention is not particularly limited.

Examples of the catalyst include a transition metal complex-based catalyst which is used for an atom transfer radical polymerization (ATRP method), a catalyst consisting of a compound containing at least one center element selected from phosphorus, nitrogen, carbon, oxygen, germanium, tin, and antimony and a halogen atom bound to the center element, which is used for reversible chain transfer catalyst polymerization (RTCP method), an organic amine compound used for reversible complexation mediated polymerization (RCMP), and a catalyst in which, as a non-metal compound having an ionic bond with a halide ion, a non-metal atom in the non-metal compound is in a cation state and forms an ionic bond with the halide ion.

As for the transition metal complex-based catalyst, a metal complex formed of a metal with a low atomic valency such as in Group 7, Group 8, Group 9, Group 10, or Group 11 of the Periodic Table and an organic ligand or a metal complex formed of a metal with a low atomic valency such as in Group 7, Group 8, Group 9, Group 10, or Group 11 of the Periodic Table, a metal with a high atomic valency, and an organic ligand (see JP 2002-249505 A) can be used.

Examples of the metal with low atomic valency include cuprous chloride, cuprous bromide, cuprous iodide, cuprous cyanide, cuprous oxide, ferrous chloride, ferrous bromide and ferrous iodide, and examples of the metal with high atomic valency include ferric chloride, ferric bromide, ferric iodide, ruthenium dichloride, ruthenium dibromide, and ruthenium diiodide.

Furthermore, examples of the organic ligand include pyridines, bipyridines, polyamines, and phosphines, and specific examples thereof include 2,2'-bipyridyl and a derivative thereof, 1,10-phenanthroline and a derivative thereof, tetramethylethylene diamine, pentamethyldiethylene triamine, tris(dimethylaminoethyl)amine, triphenylphosphine, and tributylphosphine.

Examples of the catalyst which has an element selected from germanium, tin, and antimony as a center element include a compound which contains at least one center element selected from germanium, tin, and antimony and at least one halogen atom bound to the center element, and specific examples thereof include germanium (II) iodide, germanium (IV) iodide, tin (II) iodide, and tin (IV) iodide (see, JP 2007-92014 A).

As for the catalyst in which nitrogen or phosphorus is contained as a center element, a compound having at least one center element selected from nitrogen and phosphorus and at least one halogen atom bound to the center element can be mentioned. Specific examples thereof include phosphorus halide, phosphine halide, nitrogen halide, phosphorus acid halide, amine halide, and imide halide derivative (see, WO 2008/139980 A).

Specific examples of the organic amine compound catalyst include triethylamine, tributylamine, 1,1,2,2-tetrakis(dimethylamino)ethene, 1,4,8,11-tetramethyl-1,4,8,11-tetraazacyclotetradecane, ethylenediamine, tetramethylethylenediamine, tetramethyldiaminomethane, tris(2-aminoethyl)amine, tris(2-(methylamino)ethyl)amine, and hematopporphyrin (see, WO 2011/016166 A).

Specific examples of the catalyst in which, as a non-metal compound having an ionic bond with a halide ion, a non-metal atom in the non-metal compound is in a cation state and forms an ionic bond with the halide ion include ammonium salt, imidazolium salt, pyridinium salt, phosphonium salt, sulfonium salt, and iodonium salt. More specific examples thereof include tetrabutyl ammonium iodide, tetrabutyl ammoniumtri iodide, tetrabutyl ammoniumbromo diiodide, 1-methyl-3-methyl-imidazolium iodide, 1-ethyl-3-methylimidazolium bromide, 2-chloro-1-methylpyridinium iodide, hexaphenyldiphosphagenium chloride, methyltributyl phosphonium iodide, tetraphenyl phosphonium iodide, tributylsulfonium iodide, and diphenyliodonium iodide (see, WO 2013/027419 A).

(4) Reaction Temperature

The reaction temperature is not particularly limited. It is preferably 0° C. to 180° C., and more preferably 30° C. to 120° C.

(5) Reaction Time

The reaction time can be suitably selected within a range of 30 minutes to 24 hours such that is it suitable for each reaction.

(6) Reaction Solvent

The reaction can be carried out in the absence of a solvent. However, it is also possible to use a solvent. The reaction solvent is not particularly limited as long as the reaction is not inhibited by it. However, it is preferable to use acetonitrile, methylene chloride, tetrahydrofuran, toluene, xylene, acetone, methyl ethyl ketone, ethanol, isopropanol, ethyl acetate, butyl acetate, ethyl cellosolve, or the like.

EXAMPLES

Hereinbelow, the present invention is described in greater detail in view of the Examples. However, it is evident that the present invention is not limited to the Examples at all.

<Preparation of a Living Radical Polymerization Initiator>

(Example 1) Preparation of methyl 2-iodo-2-(4'-(2"-iodopropionyloxy)phenyl)acetate

[Chemical Formula 2]

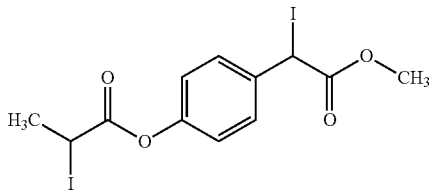

(2)

To a mixture solution of 25.00 g (150.4 mmol) of methyl 4-hydroxyphenylacetate, 47.60 g (601.7 mmol) of pyridine, and 100 mL of diethyl ether, 50 mL diethyl ether solution of 38.97 g (180.5 mmol) of 2-bromopropionyl bromide was added at 0° C.

After that, the reaction mixture was stirred for 30 minutes at room temperature and then washed with 5% hydrogen bromide, a saturated aqueous solution of sodium carbonate, a saturated aqueous solution of sodium sulfite, and water followed by extraction of an organic layer. The extracted solution was dried over anhydrous sodium sulfate, and according to concentration under reduced pressure, 42.91 g (yield: 95%) of methyl 2-(4'-(2"-bromopropionyloxy)phenyl)acetate was obtained.

Next, to 66 mL dichloroethane solution of 9.94 g (33.00 mmol) of methyl 2-(4'-(2"-bromopropionyloxy)phenyl)acetate, 7.05 g (39.60 mmol) of N-bromosuccinimide was added at room temperature, and stirred under reflux for 5 hours while being illuminated with an LED light.

The obtained reaction mixture was washed with a saturated aqueous solution of sodium sulfite and water followed by extraction of an organic layer. The extracted solution was dried over anhydrous sodium sulfate, and according to concentration under reduced pressure, 11.67 g (yield: 93%) of methyl 2-bromo-2-(4'-(2"-bromopropionyloxy)phenyl)acetate was obtained.

To 55 mL acetonitrile solution of 10.37 g (27.23 mmol) of methyl 2-bromo-2-(4'-(2"-bromopropionyloxy)phenyl)acetate, 16.35 g (109.11 mmol) of sodium iodide was added at 0° C. and then stirred at the same temperature for 1.5 hours.

The obtained reaction mixture was added with dichloromethane and then washed with a saturated aqueous solution of sodium sulfite and water followed by extraction of an organic layer.

The extracted solution was dried over anhydrous sodium sulfate and then concentrated under reduced pressure, and according to purification by silica gel column chromatography, 5.80 g (yield: 45%) of methyl 2-iodo-2-(4'-(2"-iodopropionyloxy)phenyl) acetate was obtained. $^1$H NMR (CDCl$_3$): δ=2.04 (d, 3H), 3.76 (s, 3H), 4.68 (q, 1H), 5.52 (s, 1H), 7.07 (d, 2H), 7.63 (d, 2H).

(Example 2) Preparation of 4-iodobutyl 2-iodoisobutyrate

[Chemical Formula 3]

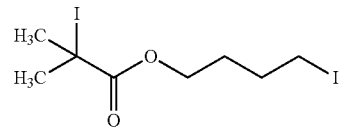

(3)

4.5 g (20 mmol) of 2-bromoisobutyric acid bromide and 9.0 g (60 mmol) of sodium iodide were admixed with each other under light-shielded condition, and after adding 4.8 mL (60 mmol) of tetrahydrofuran thereto, they were stirred for 2 hours at 25° C. and subsequently for 30 minutes at 50° C.

Next, the obtained reaction mixture was added with dichloromethane and then washed with a saturated aqueous solution of sodium sulfite. After drying over anhydrous sodium sulfate followed by concentration under reduced pressure, 20 mL of acetonitrile was added and then 6.0 g (40 mmol) of sodium iodide was added. After the reaction for 7 hours at 80° C., 9.0 g (60 mmol) of sodium iodide was added followed by further reaction for 7 hours.

After that, the precipitates were separated by filtration followed by concentration under reduced pressure. Dichloromethane was then added and washing with a saturated aqueous solution of sodium sulfite was carried out. After drying over anhydrous sodium sulfate, a concentration under a reduced pressure was carried out.

Then, by purifying the obtained crude product by silica gel column chromatography, 4.4 g (yield: 68%) of (4-iodobutyl)2-iodoisobutyric acid was obtained. 1H NMR (CDCl3): δ=4.17 (t, 2H), 3.22 (t, 2H), 2.06 (s, 6H), 1.98-1.90 (m, 2H), 1.83-1.77 (m, 2H).

(Example 3) Preparation of Methyl 2-iodo-2-(4'-(4"-iodobutanoyloxy)phenyl)acetate

[Chemical Formula 4]

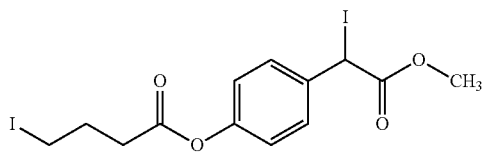

(4)

To a mixture solution of 20.00 g (120.36 mmol) of methyl 4-hydroxyphenylacetate, 22.11 g (132.39 mmol) of 4-boromobutyric acid, and 60 mL of benzene, 16.69 g (108.32 mmol) of phosphoryl chloride was added at room temperature.

After that, it was stirred for 5.5 hours at 80° C. and the reaction mixture was added to 100 mL of water to extract an organic layer. The extracted solution was washed with a saturated aqueous solution of sodium sulfite and water followed by drying over anhydrous sodium sulfate, and according to a concentration under a reduced pressure, 34.37 g (yield: 91%) of methyl 2-(4'-(4"-bromobutanoyloxy)phenyl) acetate was obtained.

To 85 mL dichloroethane solution of 26.31 g (83.48 mmol) of methyl 2-(4'-(4"-bromobutanoyloxy)phenyl)acetate, 22.29 g (125.22 mmol) of N-bromosuccinimide was added at room temperature.

Next, stirring under reflux was carried out for 6.5 hours while being illuminated with an LED light. The obtained reaction mixture was washed with a saturated aqueous solution of sodium sulfite and water followed by extraction of an organic layer.

Next, the extracted solution was dried over anhydrous sodium sulfate followed by a concentration under a reduced pressure. By purifying the obtained crude product by silica gel column chromatography, 7.29 g (yield: 22%) of methyl 2-bromo-2-(4'-(4"-bromobutanoyloxy)phenyl)acetate was obtained.

Next, to 20 mL acetone solution of 6.92 g (17.56 mmol) of methyl 2-bromo-2-(4'-(4"-bromobutanoyloxy)phenyl)acetate, 6.32 g (42.14 mmol) of sodium iodide was added at room temperature and then stirred for 0.5 hour at 40° C.

Next, the obtained reaction mixture was added with dichloromethane and washed with a saturated aqueous solution of sodium sulfite and water followed by extraction of an organic layer.

Then, the extracted solution was dried over anhydrous sodium sulfate followed by concentration under reduced pressure. The obtained crude product was purified by silica gel column chromatography to obtain 2.50 g (yield: 30%) of methyl 2-iodo-2-(4'-(4"-iodobutanoyloxy)phenyl)acetate. 1H NMR (CDCl3): δ=2.17-2.21 (m, 2H), 2.66-2.69 (t, 2H), 3.25-3.28 (t, 2H), 3.73 (s, 3H), 5.53 (s, 1H), 7.02-7.04 (m, 2H), 7.59-7.61 (m, 2H).

(Example 4) Preparation of 4-iodobutyl 2-iodophenylacetate

[Chemical Formula 5]

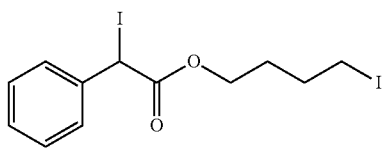

(5)

6.5 g (30 mmol) of 2-bromophenylacetic acid was mixed with 4.2 mL (60 mmol) of thionyl chloride, and under a light-shielded condition, they were stirred for 50 minutes at 80° C.

Subsequently, after removing volatile components under a reduced pressure, 8 mL (100 mmol) of THF was added and 18.0 g (120 mmol) of sodium iodide was added under light-shielded condition. After stirring for 2 hours at 27° C., 4.5 g (30 mmol) of sodium iodide was added and stirred for 5 hours at the same condition.

Next, the obtained reaction mixture was added with dichloromethane and washed with 10 mL of an aqueous solution of sodium sulfite. Furthermore, the aqueous phase was extracted with 20 mL of dichloromethane and the organic layer was combined. After drying over anhydrous sodium sulfate, a concentration under a reduced pressure was carried out.

Then, the obtained crude product was purified by silica gel column chromatography to obtain 4.1 g (yield: 31%) of 4-iodobutyl 2-iodophenyl acetate. 1H NMR (CDCl3): δ=7.59-7.57 (m, 2H), 7.33-7.27 (m, 3H), 5.18 (s, 1H), 4.21-4.14 (m, 2H), 3.18 (t, 3H), 1.92-1.86 (m, 2H), 1.81-1.76 (m, 2H).

(Example 5) Preparation of 2-(iodoacetoxy)ethyl 2-iodo-2-phenylacetate

[Chemical Formula 6]

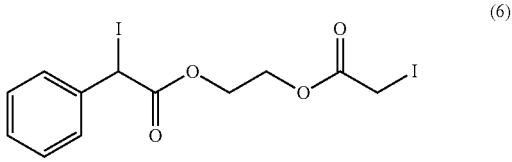

(6)

To 25.00 g (114.66 mmol) of 2-boromophenyl acetic acid, 27.28 g (229.32 mmol) of thionyl chloride was added followed by stirring under reflux of 1 hour.

After that, the remaining thionyl chloride was removed under a reduced pressure, and then added to a mixture of 284.67 g (4586.32 mmol) of ethylene glycol and 9.52 g (120.39 mmol) of pyridine at room temperature.

After stirring at the same temperature for 1 hour, diethyl ether was added and washing was carried out with 1 N hydrochloric acid, a saturated aqueous solution of sodium carbonate and water.

After drying over anhydrous sodium sulfate, 23.61 g (yield: 80%) of 2-hydroxyethyl 2-bromo-2-phenylacetate was obtained.

To a mixture of 5.00 g (19.30 mmol) 2-hydroxyethyl 2-bromo-2-phenylacetate, 1.60 g (20.26 mmol) of pyridine, and 20 mL of diethyl ether, 10 mL diethyl ether solution of 4.09 g (20.26 mmol) of 2-bromopropionyl bromide was added at room temperature.

After stirring at the same temperature for 1 hour, the obtained reaction mixture was washed with 5% hydrogen bromide, a saturated aqueous solution of sodium carbonate and water to extract an organic layer.

The extracted solution was dried over anhydrous sodium sulfate followed by concentration under reduced pressure. The obtained crude product was purified by silica gel column chromatography to obtain 4.41 g (yield: 60%) of 2-(bromoacetoxy)ethyl 2-bromo-2-phenyl acetate.

To 22 mL acetone solution of 4.25 g (11.18 mmol) of 2-(bromoacetoxy)ethyl 2-bromo-2-phenyl acetate, 4.02 g (26.83 mmol) of sodium iodide was added at 0° C. followed by stirring at the same temperature for 30 minutes.

After that, the precipitates were separated by filtration followed by concentration under reduced pressure. Dichloromethane was then added and washing with a saturated aqueous solution of sodium sulfite and water was carried out and an organic layer was extracted.

Then, the extracted solution was dried over anhydrous sodium sulfate followed by a concentration under a reduced pressure. The obtained crude product was purified by silica gel column chromatography to obtain 2.52 g (yield: 48%) of 2-(iodoacetoxy)ethyl 2-iodo-2-phenylacetate. $^1$H NMR (CDCl3): δ=3.66 (s, 2H), 4.34-4.38 (m, 4H), 5.55 (s, 1H), 7.28-7.33 (m, 3H), 7.58-7.60 (m, 2H).

<Production of Polymer>

Figure 2:
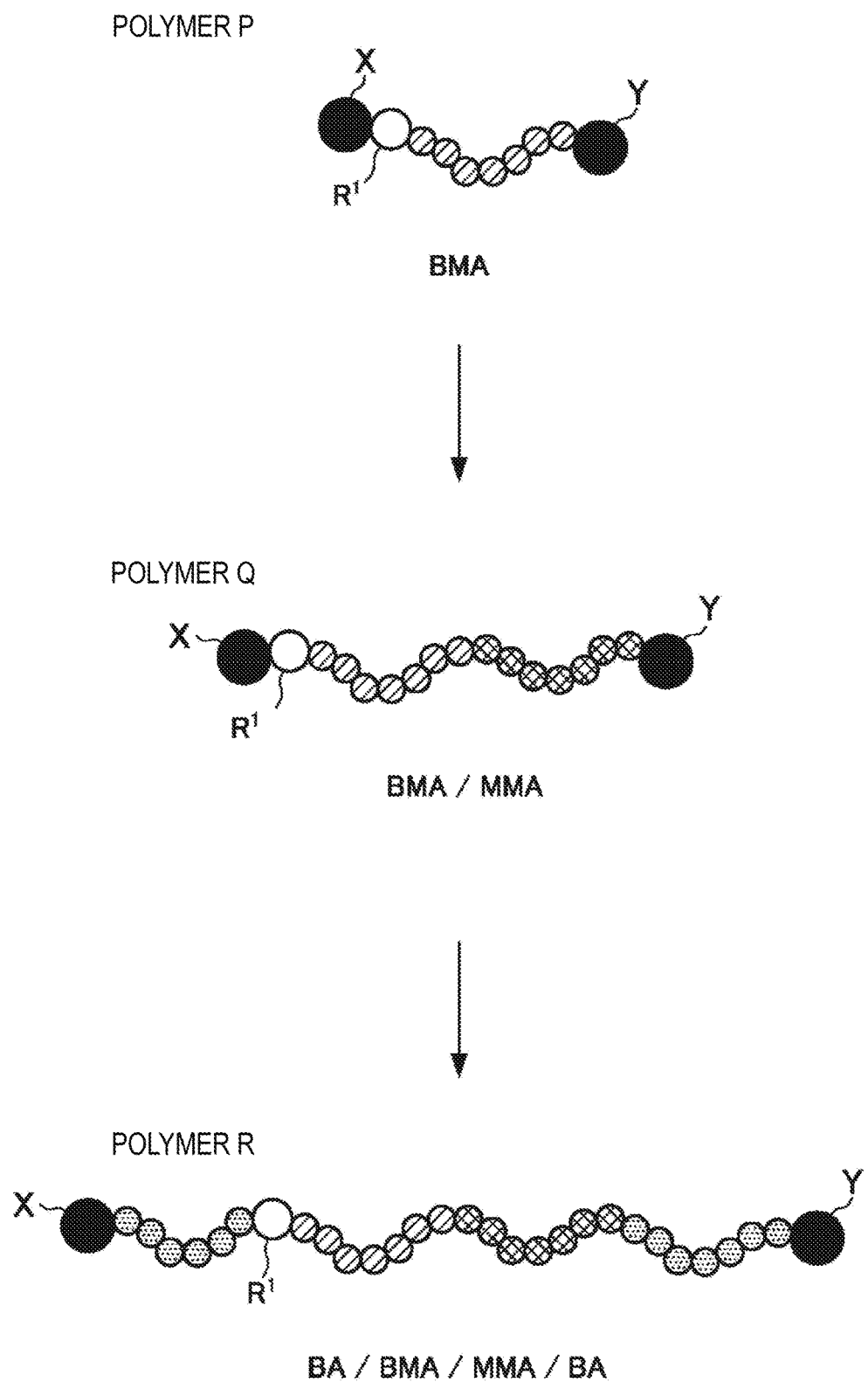
FIG. 2 is a schematic diagram illustrating a process for having a polymer with regard to a method for producing a polymer according to Example.
Figure 3:
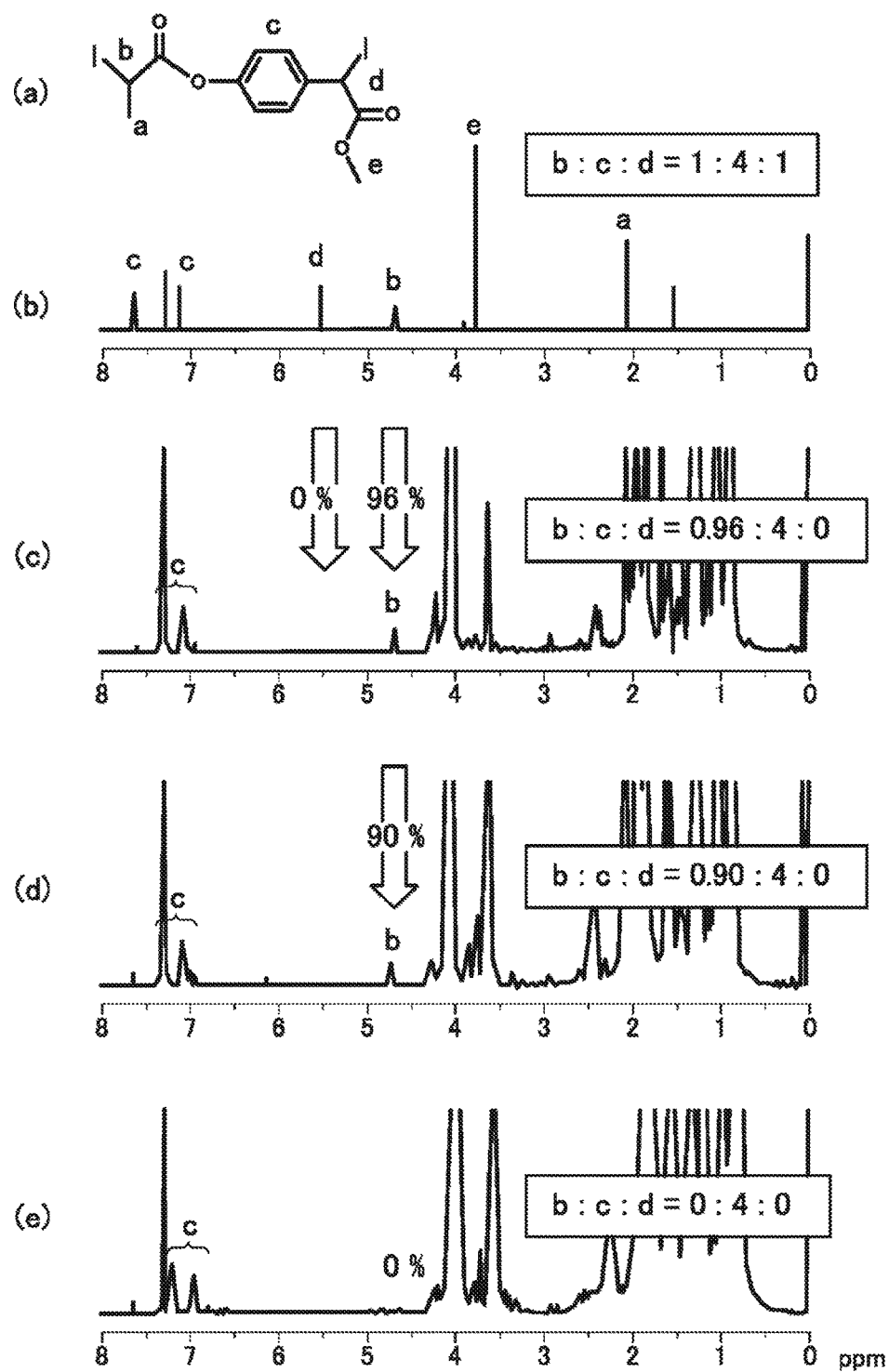
FIG. 3 is a 1H-NMR chart of a living radical polymerization initiator and each polymer obtained by the method for producing a polymer according to Examples, in which (a) represents a structural formula of an alkyl iodide as a living radical polymerization initiator, (b) represents a 1H-NMR chart of the living radical polymerization initiator, (c) represents a 1H-NMR chart of a polymer P, (d) represents a 1H-NMR chart of a polymer Q, and (e) represents a 1H-NMR chart of a polymer R.

Based on the basic reaction described above, production of a living radical polymer was carried out under the following specific reaction conditions. FIG. 2 is a schematic diagram illustrating a process for having a polymer with regard to a method for producing a polymer according to Example. FIG. 3 is a 1H-NMR chart of a living radical polymerization initiator and each polymer obtained by the method for producing a polymer according to Example, in which (a) represents a structural formula of alkyl iodide as a living radical polymerization initiator, (b) represents a 1H-NMR chart of the living radical polymerization initiator, (c) represents a 1H-NMR chart of a polymer P, (d) represents a 1H-NMR chart of a polymer Q, and (e) represents a 1H-NMR chart of a polymer R.

In the method for producing a polymer according to this Example, all the polymerization reactions were carried out under an argon gas atmosphere.

To 20 mL (8 M) of butyl methacrylate (BMA), methyl 2-iodo-2-(4'-(2"-iodopropionyloxy)phenyl)acetate (160 mM) and tributylmethyl phosphonium iodide (80 mM) were added and then stirred under heating for 8 hours at 60° C. The polymerization rate (i.e., monomer conversion rate) was 55%.

To chilled hexane, the reaction solution was added and the polymer was isolated by re-precipitation. The isolated polymer P has a Mn=3,900 and a PDI=1.15. According to the NMR measurement, the iodophenyl acetyl part had undergone almost 100% initiation of the polymerization to have a grown polymer. On the other hand, 96% of the iodopropionyl part had no initiation and almost selective growth of a polymer of BMA from the iodophenyl acetyl part was shown.

To the polymer P (160 mM), 20 mL (8M) of methyl methacrylate (MMA) and tributylmethyl phosphonium iodide (80 mM) were added and then stirred under heating for 8 hours at 60° C. The polymerization rate (i.e., monomer conversion rate) of MMA was 30%.

To chilled hexane, the reaction solution was added and the polymer was isolated by re-precipitation. The isolated polymer Q has a Mn=5,800 and a PDI=1.24. According to the NMR measurement, 90% of the iodopropionyl part had no initiation and a block polymer (BMA and MMA) was almost selectively produced from the iodophenyl acetyl part.

Furthermore, to the polymer Q (160 mM) obtained in the second reaction step, 20 mL (8 M) of n-butyl acrylate (BA) and tetrabutyl ammonium iodide (320 mM) were added and then stirred under heating for 24 hours at 110° C. The polymerization rate (i.e., monomer conversion rate) of BA was 32%. To chilled hexane, the reaction solution was added and the polymer was isolated by re-precipitation.

The isolated polymer R has a Mn=8,000 and a PDI=1.33. According to the NMR measurement, the polymerization was initiated almost 100% from of the iodopropionyl part. Accordingly, together with growth of a homopolymer of BA, a triblock polymer (BMA, MMA, and BA) was grown from iodophenyl acetyl part.

Accordingly, it was possible to synthesize a non-symmetric multi-block polymer of CABC type in which A chain is BMA, B chain is MMA, and C chain is BA.

A 1H-NMR chart of the polymer P, Q, and R which have been obtained in each step is as shown in (c) to (e) of FIG. 3, respectively.

Incidentally, "M" with regard to the concentration indicates a mole number based on 1 liter of a monomer. For example, 8 M means that 8 moles are included in 1 liter of a monomer. Incidentally, in case of MMA, 1 liter of a monomer (in bulk) is 8 moles at room temperature.

Furthermore, "mM" with regard to the concentration indicates a millimole number based on 1 liter of a monomer. For example, 80 mM means that 80 millimoles are included in 1 liter of a monomer.

Furthermore, "Mn" indicates a number average molecular weight of an obtained polymer.

Furthermore, "PDI" indicates the ratio of Mw/Mn.

According to the method for producing a polymer of the present invention described in the above, since a living radical polymerization initiator which has, as an initiating group for reaction, two halogen atoms different from each other in reactivity is used, it is possible to proceed with a different living radical polymerization reaction for each initiating group by suitably adjusting the reaction conditions.

REFERENCE SIGNS LIST $R^1$ Linking group $R^2$ Any one of a halogen atom, an aromatic group, an aliphatic group, and an acyloyl group X, Y Halogen atom

The invention claimed is:

1. A method for producing a polymer, comprising:
(i) carrying out a first polymerization step comprising mixing a living radical polymerization reaction initiator with a first monomer having an unsaturated bond at reaction conditions to initiate a living radical polymerization reaction, the living radical polymerization initiator being represented by the following formula (1):

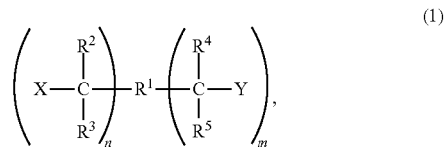

wherein in the formula (1), $R^1$ represents a substituted or unsubstituted organic group having a valency of two or more, and is selected from the group consisting of an aliphatic group having 1 to 12 carbon atoms, an aromatic group, an alkylcarbonyl group having 1 to 12 carbon atoms, an alkoxycarbonyl group having 1 to 12 carbon atoms, an aminocarbonyl group, an alkylaminocarbonyl group having 1 to 12 carbon atoms, a dialkylaminocarbonyl group having 1 to 12 carbon atoms, an arylcarbonyl group, an alkylsulfonyl group having 1 to 12 carbon atoms, an aryl sulfonyl group and an organic group in which two or more of said groups are combined, $R^2$, $R^3$, $R^4$ and $R^5$ are a hydrogen atom or a substituted or unsubstituted organic group selected from the group consisting of an aliphatic group having 1 to 12 carbon atoms, an aromatic group, an alkylcarbonyl group, an alkoxycarbonyl group, an aminocarbonyl group, an alkylaminocarbonyl group, a dialkylaminocarbonyl group having 1 to 12 carbon atoms, an arylcarbonyl group, a carboxy group, an alkylsulfonyl group having 1 to 12 carbon atoms and an aryl sulfonyl group, X and Y are each a halogen atom, m and n are an integer of 1 or more, and

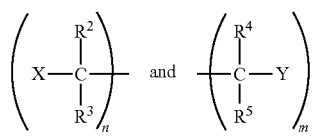

are non-symmetrical so that X and Y have different reactivities to initiate a living radical polymerization, wherein one of halogen atoms X and Y is reacted to obtain a first polymer product having at one end thereof the other of the halogen atoms X and Y which is unreacted and which is attached to the following skeleton structure:

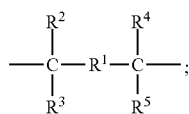

and (ii) carrying out a second polymerization step comprising mixing the first polymer product with a second monomer at reaction conditions to initiate a living radical polymerization reaction to obtain a polymer having at one end thereof one of the halogens X and Y and having at an opposite end thereof the other of the halogens X and Y, and disposed therebetween polymerized monomers and the following skeleton structure:

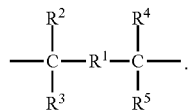

2. The living radical polymerization initiator according to claim 1, wherein the halogen atom is iodide, chloride, or bromide.

3. The method for producing a polymer according to claim 1, wherein the first polymerization step and the second polymerization step are carried out in the presence of a catalyst, and the first polymerization step and the second polymerization step are carried out such that at least one of reaction temperature and type of the catalyst is changed depending on the type of the monomer.

4. The method for producing a polymer according to claim 3, wherein the catalyst is (i) a transition metal complex-based catalyst which is operable for an atom transfer radical polymerization; (ii) a catalyst consisting of a compound containing at least one center element selected from the group consisting of phosphorus, nitrogen, carbon, oxygen, germanium, tin and antimony, and a halogen atom bound to the center element, which is operable for reversible chain transfer catalyst polymerization; (iii) an organic amine compound catalyst which is operable for a reversible complexation mediated polymerization; (iv) or a catalyst comprising a non-metal compound having an ionic bond with a halide ion, wherein a non-metal atom in the non-metal compound is in a cationic state and forms the ionic bond with the halide ion.

5. The method for producing a polymer according to claim 1, wherein the first polymerization step and the second polymerization step are each carried out at a temperature of 180° C. or lower.

6. The method for producing a polymer according to claim 1, wherein the first polymerization step and the second polymerization step are each carried out for a reaction time of 30 minutes to 24 hours.

7. The method for producing a polymer according to claim 1, further comprising, before the second polymerization step, carrying out one or more living polymerization reactions with one or more third monomers at reaction conditions to carry out a living polymerization reaction.

8. The method for producing a polymer according to claim 1, wherein the first monomer and the second monomer are different from each other and are selected from the group consisting of methyl methacrylate, ethyl methacrylate, propyl methacrylate, n-butyl methacrylate, t-butyl methacrylate, hexyl methacrylate, 2-ethylhexyl methacrylate, nonyl methacrylate, benzyl methacrylate, glycidyl methacrylate, cyclohexyl methacrylate, lauryl methacrylate, n-octyl methacrylate, 2-methoxyethyl methacrylate, butoxyethyl methacrylate, methoxytetraethylene glycol methacrylate, 2-hydroxyethyl methacrylate, 2-hydroxypropyl methacrylate, 3-chloro-2-hydroxypropyl methacrylate, tetrahydrofurfuryl methacrylate, 2-hydroxy 3-phenoxypropyl methacrylate, diethylene glycol methacrylate, polyethylene glycol methacrylate and 2-(dimethylamino)ethyl methacrylate.

9. The method for producing a polymer according to claim 1, wherein the first monomer and the second monomer are different from each other and are selected from the group consisting of methyl acrylate, ethyl acrylate, propyl acrylate, n-butyl acrylate, t-butyl acrylate, hexyl acrylate, 2-ethylhexyl acrylate, nonyl acrylate, benzyl acrylate, glycidyl acrylate, cyclohexyl acrylate, lauryl acrylate, n-octyl acrylate, 2-methoxyethyl acrylate, butoxyethyl acrylate, methoxytetraethylene glycol acrylate, 2-hydroxyethyl acrylate, 2-hydroxypropyl acrylate, 3-chloro 2-hydroxypropyl acrylate, tetrahydrofurfuryl acrylate, 2-hydroxy 3-phenoxypropyl acrylate, diethylene glycol acrylate, polyethylene glycol acrylate, and 2-(dimethylamino)ethyl acrylate.

10. The method for producing a polymer according to claim 1, wherein the living radical polymerization initiator is selected from the group consisting of methyl 2-iodo-2-(4'-(2"-iodopropionyloxy) phenyl) acetate, 4-iodobutyl 2-iodoisobutyrate, methyl 2-iodo-2-(4'-(4"-iodobutanoyloxy) phenyl) acetate, 4-iodobutyl 2-iodophenylacetate and 2-(iodoacetoxy) ethyl 2-iodo-2-phenylacetate.

11. The method for producing a polymer according to claim 3, wherein the catalyst is tributylmethyl phosphonium iodide.

* * * * *